(12) United States Patent
Striemer et al.

(10) Patent No.: US 7,692,798 B2
(45) Date of Patent: Apr. 6, 2010

(54) METHOD FOR BIOMOLECULAR DETECTION AND SYSTEM THEREOF

(75) Inventors: Christopher C. Striemer, Rochester, NY (US); Andrew J. Murnan, Saratoga Springs, NY (US); Nestor O. Farmiga, Rochester, NY (US)

(73) Assignee: Adarza Biosystems, Inc., Rochester, NY (US)

( * ) Notice: Subject to any disclaimer, the term of this patent is extended or adjusted under 35 U.S.C. 154(b) by 166 days.

(21) Appl. No.: 11/855,559

(22) Filed: Sep. 14, 2007

(65) Prior Publication Data

US 2008/0068615 A1 Mar. 20, 2008

Related U.S. Application Data

(60) Provisional application No. 60/844,842, filed on Sep. 15, 2006.

(51) Int. Cl.
*G01B 11/02* (2006.01)
(52) U.S. Cl. ...................................... 356/504
(58) Field of Classification Search ................ 356/451, 356/456, 503, 504
See application file for complete search history.

(56) References Cited

U.S. PATENT DOCUMENTS

| 6,678,308 | B1 | 1/2004 | Matthews |
| 2006/0063178 | A1 | 3/2006 | Rauh-Adelmann et al. |

FOREIGN PATENT DOCUMENTS

| WO | WO 02/068957 | 9/2002 |
| WO | WO 02/093145 | 11/2002 |
| WO | WO 03/036225 | 5/2003 |
| WO | WO 03/064995 | 8/2003 |
| WO | WO 03/065041 | 8/2003 |
| WO | WO 2006/020517 | 2/2006 |

OTHER PUBLICATIONS

International Search Report and Written Opinion of the International Searching Authority, dated Mar. 20, 2008, issued in corresponding International Patent Appl. No. PCT/US07/78515 (8 pages).

*Primary Examiner*—Michael A Lyons
(74) *Attorney, Agent, or Firm*—Dominic P. Ciminello, Esq.; Stephen B. Salai, Esq.; Harter Secrest & Emery LLP (57) ABSTRACT

A method of sensing at least one target on a receptor having a substrate and a translucent coating includes minimizing interference fringe patterns in an image of the target. The method also includes passing the image of the target through an imaging system intermediate the receptor and a detector.

31 Claims, 5 Drawing Sheets

METHOD FOR BIOMOLECULAR DETECTION AND SYSTEM THEREOF

PRIORITY INFORMATION

The present application claims the benefit of U.S. Provisional Application No. 60/844,842, filed Sep. 15, 2006. The present application expressly incorporates by reference, U.S. Publication No. 2003/0112446, published Jun. 19, 2003 (U.S. application Ser. No. 10/282,274, filed Oct. 28, 2002).

FIELD OF THE INVENTION

The present invention generally relates to biomolecular detection and a system thereof and, more particularly, to locating an imaging system optically intermediate an illuminated receptor and a detector, wherein the receptor is illuminated with coherent light.

BACKGROUND OF THE INVENTION

Technologies capable of biological sensing can offer substantial advances in the medical diagnostics field by introducing the capacity to detect molecular targets in a label-free and rapid format. Current methods used for biological sensing utilize fluorescence, calorimetric, or surface plasmon resonant techniques as indicators of a successful molecular recognition event and are thus not amenable for use by non-technical operators.

While these methods are main-stream in their respective adoption for the molecular diagnostics arena, they are not without functional limitation. For fluorescence monitoring and Enzyme Linked Immunosorbent Assay [ELISA], superfluous tags must be conjugated to the desired target through the mechanism of additional labeled antibodies, thus adding necessary complexity and cost. Colorimetric assays require the generation of a color change, often mediated via an enzymatic mechanism, and are thus non-ideal for generating high density arrays.

Miller et al. in PCT Application WO 03/036225 A1, filed May 1, 2003, sets forth a device that enables the label-free detection of biomolecules. The Miller sensing system is functionally bipartite and is comprised of: 1) a receptor for at least one target, the receptor including a substrate and a transparent coating on the substrate having front and back surfaces; and 2) a light source positioned to direct at least a portion of the light from the light source toward the coating on the receptor; and a detector positioned to capture the light reflected from the front and back surfaces of the coating, where the detector identifies the presence of at least one target based on the change in the interference pattern of the captured light.

However, the Miller system does not lend itself to quantitative detection of biomolecules in high density receptor arrays. Therefore, the need remains for the label-free detection of biomolecules, wherein a resulting image allows for quantitative analysis.

SUMMARY OF THE INVENTION

The present system generally includes the light-source and detection system, wherein the present system compensates for diffraction patterns intrinsic to the reflected signal from the receptor. Particularly, the present system removes fringe patterns from the image of the receptor. By minimizing higher order diffraction patterns and fringes, the present system enhances intensity determination and hence, allows for the quantitative detection of biomolecules at the receptor in a highly multiplexed format.

In an exemplary embodiment of the present disclosure, a method of sensing at least one target on a receptor having a substrate and a translucent coating includes minimizing interference fringe patterns in an image of the target. The method also includes passing the reflected signal of the target through an imaging lens or optical system intermediate the receptor and a detector.

In another exemplary embodiment of the present disclosure, a method of sensing at least one target on a receptor having a substrate and a translucent coating includes compensating for diffraction effects in an image of the target. The method also includes passing the image of the target through an imaging lens or optical system intermediate the receptor and a detector.

In a further exemplary embodiment of the present disclosure, an apparatus for imaging a receptor on a substrate having a translucent coating includes a coherent light source generating a coherent beam along a beam path, and a receptor disposed in the beam path to reflect the beam, the receptor forming a reflected beam along the beam path. The apparatus also includes a detector located in the beam path to image the reflected beam and an imaging lens or optical system in the beam path optically intermediate the receptor and the detector.

The accompanying drawings are included to provide a further understanding of the invention, and are incorporated in and constitute a part of this specification. The drawings are not necessarily to scale, and sizes of various elements may be distorted for clarity. The drawings illustrate one or more embodiment(s) of the invention and, together with the description, serve to explain the principles and operation of the invention.

DETAILED DESCRIPTION OF THE INVENTION

Figure 1:
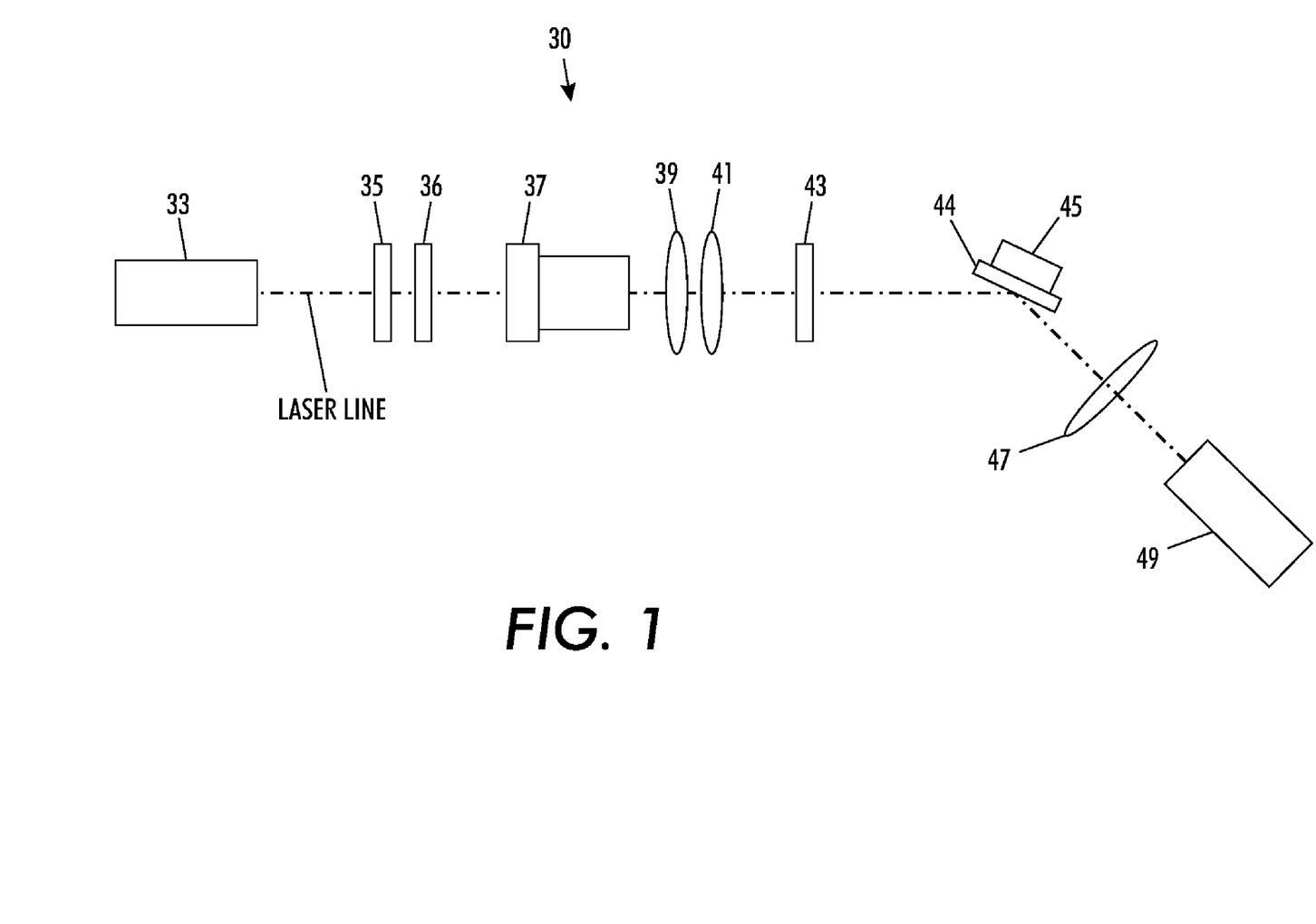
FIG. 1 is a block diagram of a biomolecular detection system in accordance with an exemplary embodiment of the present disclosure.

FIG. 1 illustrates a biomolecular detection system 30 according to an exemplary embodiment of the present disclosure. The system 30 includes a laser source 33, an aperture 35, an optical cutoff or laser line (notch) filter 36, a spatial filter comprised of an objective 37 and an optical pinhole 39, a collimating lens 41, a linear polarizer 43, a receptor mount 45, an imaging lens 47, and an optical detector 49 with multiple sensing elements.

The present system provides an improvement to the system described within Miller et al. for detection of molecular adsorption based on simple reflectivity. While the present configuration is set forth in terms of the recited components, it is understood, certain permutations of these components could also lead to other configurations resulting in an operably equivalent devices. That is, the present description is merely exemplary of the present system 30, and is intended to provide an overview or framework for understanding the nature and character of the invention.

Referring to FIG. 1, the laser source 33 may be any gas laser known in the art. The laser source 33 in the detection system 30 generates and transmits monochromatic light towards the surface of a receptor 44 supported by the receptor mount 45. In this exemplary embodiment, the laser source 33 is a collimated monochromatic light source that is tunable or not tunable. That is, the wavelength of the generated beam can be varied by any of a number of mechanisms known in the art. Alternative light sources such as a laser diode, a DFB laser source, or a lamp with a narrow bandpass filter could also be used. The medium in which the light travels from the laser source 33 to the substrate holder 45 could be air, an optical fiber 32 (FIG. 1a), an aqueous solution, or any other waveguide material known in the art.

The aperture 35 is configured to remove substantially all stray radiation generated by laser source 33. It is understood that the light emitted by the laser source 33 can be highly collimated, thus, the resulting beam can be extremely thin with very little divergence. A cavity (not shown) of the laser source 33 can include substantially parallel anterior and posterior mirrors configured to constrain the emitted laser beam to a path which is substantially perpendicular to the mirrors. The anterior mirror can be approximately 100% reflective while the posterior mirror can be approximately 99% reflective, such that approximately 1% of the beam can be emitted by the laser source 33. This emitted beam is represented by the laser line illustrated in FIG. 1. Thus, it is understood that the light can pass back and forth between the anterior and posterior mirrors of the laser source 33 to gain intensity by the stimulated emission of additional photons at the same wavelength. If the reflected light is even slightly off axis, it will be lost from the resulting emitted beam (the laser line). Thus, in the event that the beam emitted from the laser source 33 is not completely collimated, the aperture 35 can be configured to remove any divergent portions thereof.

Optical cutoff or laser line (notch) filter 36 can be configured to remove superfluous background radiation generated by laser source 33 at wavelengths other than that of the desired wavelength. The beam emitted by the laser source 33 can be produced by a single atomic transition and can, thus, have a single precise wavelength. Such a beam can have a single spectral color and can be almost purely monochromatic. The spectral emission line from which the emitted beam originates, however, may not have a finite width. This variance in width can be caused by a number of factors, including the Doppler effect of the moving atoms or molecules from which the beam originates. Since the wavelength of the emitted beam is relatively small compared to the overall size of the cavity of the laser source 33, many resonant modes of the cavity can exist within the tiny spectral bandwidth of the emitted beam. The laser line filter 36 can be configured to effectively cutoff the variant spectral portions of the emitted beam. In an exemplary embodiment, the optical cutoff filter 36 can be used in conjunction with a laser source 33 such as, for example, a diode laser having a high bandwidth. In a further exemplary embodiment wherein a narrow bandwidth laser source 22 such as, for example, a DFB laser is used, the optical cutoff filter 36 can be omitted.

The objective 37 can be, for example, a spatial filter such as, but not limited to, a microscope objective. The optical pinhole 39 can be disposed at the focal point of objective 37 and can be configured to substantially remove nonuniformities in the intensity of the beam generated by the laser source 33. It is understood that the intensity of a beam is the absolute measure of the light wave's power density. Accordingly, the optical pinhole 39 can be configured to assist in creating a uniform and expanded beam profile. It is also understood that the output of an optical fiber can itself be considered a point source (pinhole). The expanding beam that emerges from such a fiber can have a highly uniform profile. It is further understood that the objective 37 need not be self contained. The objective can be comprised of a single aspheric lens or a series of lenses configured to focus and/or expand a diameter of an incoming light beam to a desired pre-defined diameter.

The collimating lens 41 can be any lens, lens system, or other optical device configured to calibrate the pointing and focus of an optical imaging system. As used in the system 30 of the present disclosure, the collimating lens 41 can be configured to recollimate the beam emitted by the laser source 33 and exiting the optical pinhole 39, to ensure parallel propagation of the beam radiation incident on receptor 44. It is understood that forming a well collimated parallel propagating beam insures that substantially all optical rays are incident on the receptor 44 at the same angle. Variability of incident angles can be a source of error in the system 30. Thus, in an exemplary embodiment, the system 30 can include all-reflective elements, such as, for example, mirrors configured to substantially eliminate the interference effects associated with multiple reflections from the surfaces of transparent refractive optical elements (i.e., lenses).

As illustrated in FIG. 1, the linear polarizer 43 can be disposed substantially within the path of the laser line and can be configured to polarize the beam emitted from the laser source 33 in a single direction. The polarizer 43 can be any optical component known in the art capable of assisting in converting an unpolarized or mixed-polarization beam of electromagnetic waves into a beam with a single polarization state. The polarizer 43 can be, for example, an absorptive polarizer or a beam-splitting polarizer. In an exemplary embodiment, the polarizer 43 can be configured to remove p-wave component and ensure pure s-wave polarization of the beam generated by the laser source 33 and incident to receptor 44. In an exemplary embodiment, the effective elimination of the p-polarized light component can increase the sensitivity of the detection system 30.

Although not shown in FIG. 1, in an exemplary embodiment, the system 30 can include a rotational driving device connected to the polarizer 43 and configured to rotate the polarizer 43 about an axis defined by the laser line. Rotating the polarizer 43 can enable the ratio of p-polarized to s-polarized light to be measured, thereby providing an internal reference that can be utilized to further improve the accuracy of the system 30. In a further exemplary embodiment, a polarized light source or polarizing optical fiber can be used instead of the non-polarized laser source 33. In such an embodiment, the polarizer 43 can be omitted.

The receptor 44 can be any substrate known in the art and the receptor 44 can be disposed or otherwise positioned in the path of the polarized light emitted by the polarizer 43. In an exemplary embodiment, light can be emitted by the laser source 33 so as to intersect the receptor 44 at a desired angle. In an exemplary embodiment, components of the systems described herein such as, for example, the detector 49, can be mounted, angled, tilted and/or otherwise disposed at an angle relative to the beam emitted by the laser source 33. The receptor 44 can include a surface receptive to the adsorption of one or more targets. In an exemplary embodiment, the receptor 44 can comprise a substrate that is substantially covered with a coating or array of various coatings across the surface. The substrate can be made from any conventional substrate material known in the art such as, for example, glass, silicon, and other like materials.

The coating can be a single layer of material or, alternatively, can be a plurality of layers of material. Such materials can include, for example, silicon dioxide (glass), silicon nitride, any known polymer, and an evaporated molecular material. In an exemplary embodiment, the coating can be functionalized to include probe molecules specific for a desired target molecule. In such an exemplary embodiment, a layer of the coating can be silicon dioxide and the coating can be configured to include a further adsorbate that is receptive to adsorption of one or more targets of a biological sample applied thereto. In an exemplary embodiment, the coating can include antibodies and/or other proteins. In each of the above exemplary embodiments, the coating of the receptor 44 can be substantially non-reflective.

In an exemplary embodiment, the coating can comprise a front surface and a back surface. The front surface can be the surface presented to the beam emitted by the polarizer 43 and the back surface can be the surface of the coating in contact with the substrate. The front and back surfaces of the coating can be configured to reflect incidental light and, as will be described in greater detail below, the front and back surface reflections can result in a measurable amount of destructive interference. The adsorbing target biomolecules can effectively change the coating thickness to afford a change in the destructive interference pattern of the reflected light.

The receptor support 45 is configured to rigidly hold the receptor 44 in place with minimal movement for imaging on the detector 49. The receptor support 45 can be disposed substantially behind the receptor 44 such that it can be occluded from the laser line by the receptor 44. Disposing the receptor support 45 in this way serves to reduce and/or substantially prevent the creation of optical artifacts by the receptor support 45. The receptor support 45 can comprise any support structures known in the art such as, for example, vacuum chucks, brackets, mounting plates, clips, beams, and the like. It is understood that the receptor support 45 can also include any conventional structures or means to facilitate a rigid, substantially permanent connection between the receptor support 45 and the receptor 44 such as, for example, vacuum, clamps, adhesives, bolts, screws, and other like structures.

As shown in FIG. 1, the imaging lens 47 can be disposed optically intermediate the illuminated receptor 44 and the detector 49. The imaging lens 47 can be any optical lens, or optical system (refractive or reflective in nature) known in the art configured to desirably focus one or more beams of light. The imaging lens 47 can be any size and/or shape known in the art, and the imaging lens 47 can be configured to compensate for diffraction effects in the propagating (reflected) beam received from the receptor 44. Without compensation from the imaging lens 47, individual spots in the resulting image are washed out by interference patterns and cannot be quantitatively analyzed. This compensation effect can be achieved with a single imaging lens 47 or by a collection of imaging elements 47a, 47b (discussed in greater detail below with respect to FIG. 1a), and the compensation effect facilitated by the imaging lens 47 can enhance image clarity as measured by the detector 49 disposed downstream thereof. For example, as illustrated in FIG. 2, even with a highly collimated illumination source, an imaging lens 47 may still be required to compensate for diffraction effects. The known practice of simply collecting the reflected light with an arrayed detector, on the other hand, can yield poor results that are often not useful.

The detector 49 illustrated in FIG. 1 is disposed and/or otherwise configured to measure the reflected light from the receptor 44 downstream of the imaging lens 47. The detector 49 can include any reflected beam measurement device known in the art such as, for example, a spectrometer. The detector 49 can be configured to measure the amplitude of the reflected light at a single polarization (i.e., the intensity pattern resulting from reflection of the beam off of the receptor 44), and the detector 49 can be configured to ignore phase. The detector 49 can include an array of optical detection elements to assist in measuring the intensity pattern of the reflected beam. In an exemplary embodiment of the present disclosure, the detector 49 can include a charge couple device (CCD) imaging device, a complementary metal oxide semiconductor (CMOS) imaging device, or other detection devices, wherein the detection devices can include multiple sensing elements (1 or 2 dimensional). The interference between reflected light from the front and back coating surfaces of the receptor 44 can be sensed and/or otherwise measured by the detector 49, and a change in the interference pattern afforded by a particular coating results from adsorption of a target molecule to the coating surface thereby increasing the effective thickness of the coating.

Although illustrated in block diagram format in FIG. 1, as discussed above, the detector 49 can be disposed at, for example, an oblique angle relative to a laser beam received by the detector 49. Such a configuration is more clearly shown by the angle b in FIG. 1a. It is understood that in each of the exemplary embodiments of the present disclosure, a sensing element of the detector 49 can be disposed at an oblique angle relative to a laser beam received by the detector 49.

It is understood that tilting the detector 49 to image the reflected beam obliquely can result in several advantages. For example, if the incident angle of the detector 49 matches that of the image formed by the system 30, the entire receptor 44 can be sharply imaged. Such a process is known as diffraction limited imaging. The image formed may never be perfectly perpendicular to the beam because the beam strikes the receptor 44 at a non-normal incident angle. In addition, if the detector 49 is tilted to approximately its Brewster angle, and the polarization of the light is p-wave relative to the detector 49, no additional antireflective coatings will need to be integrated into the detector 49, as reflection will intrinsically be minimized.

Figure 1A:
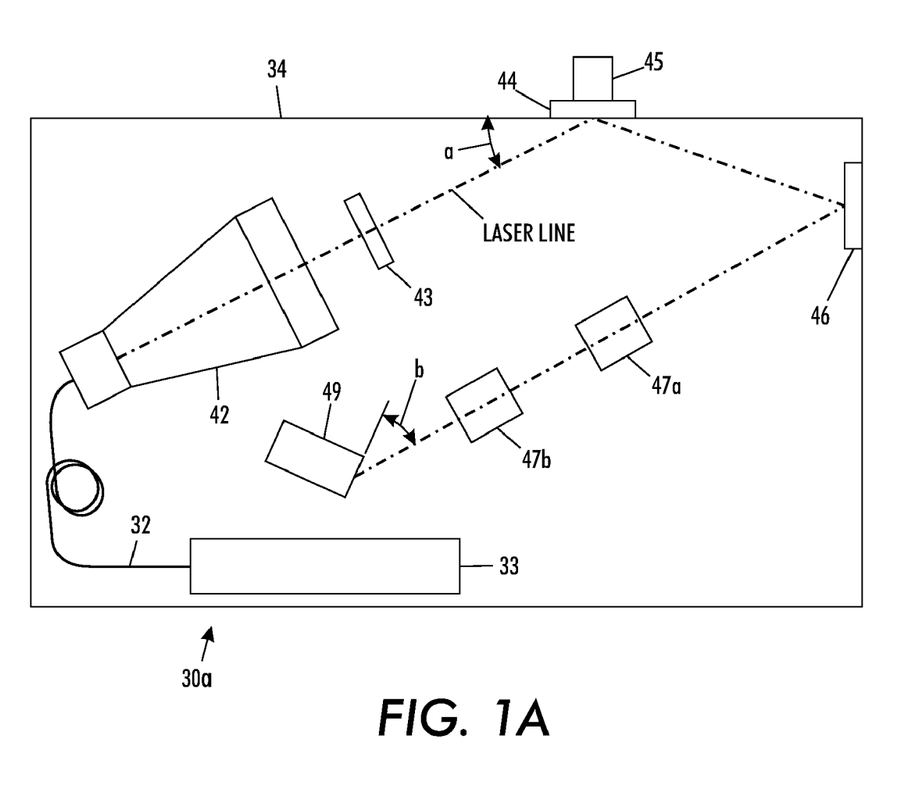
FIG. 1a is a block diagram of a biomolecular detection system in accordance with another exemplary embodiment of the present disclosure.
Figure 2:
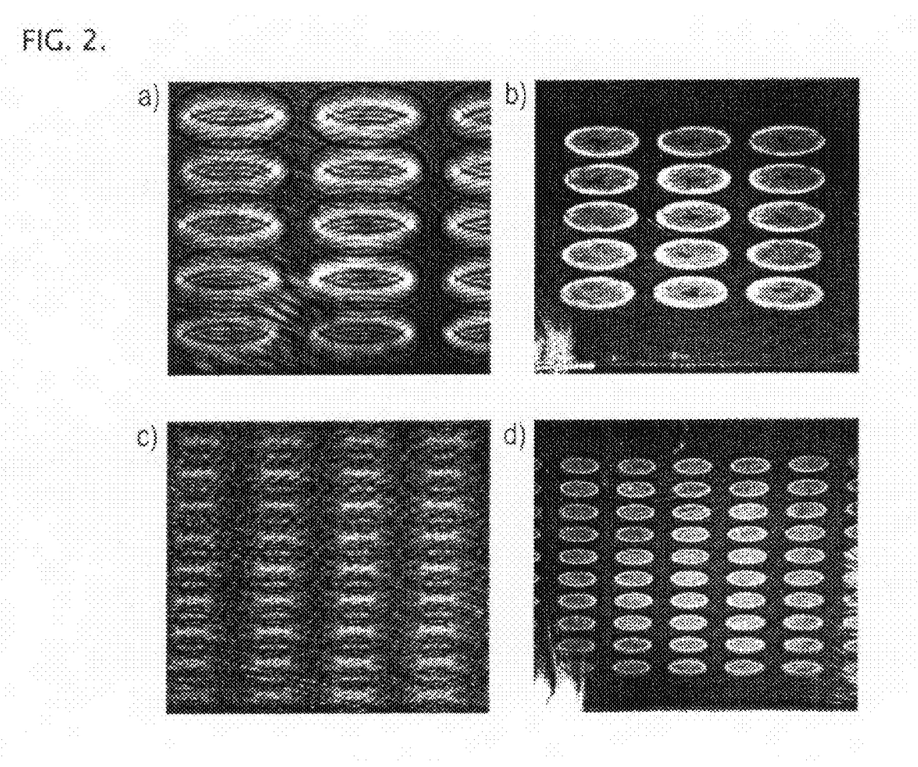
FIG. 2 demonstrates the present improvement of the array resolution and sensitivity.

FIG. 1a illustrates a biomolecular detection system 30a according to an additional exemplary embodiment of the present disclosure. Where possible, like reference numbers have been used to identify components of the system 30a that correspond to similar components of the system 30 illustrated in FIG. 1. The system of FIG. 1a is contained substantially within a housing 34. The housing can be made from any metal or alloy, plastic or composite known in the art and, in an exemplary embodiment, the housing 34 can be made from anodized aluminum. The housing 34 can be relatively lightweight but can be rigid enough to support and/or protect components of the system 30a bolted and/or otherwise connected thereto.

As shown in FIG. 1a, the system 30a can include, for example, a laser source 33 connected to a fiber collimator 42 by an optical fiber 32. the system 30a can also include a polarizer 43 downstream of the collimator 42, a receptor 44 mounted incident to and/or otherwise in the path of a laser line exiting the polarizer 43, and a fold mirror 46 positioned to intercept the laser line reflected off of the receptor 44. The system 30a can also include imaging optics 47a, 47b positioned to intercept the laser line reflected off of the fold mirror 46 and a detector downstream of the imaging optics 47a, 47b.

In an exemplary embodiment, the laser source 33 of FIG. 1a can be, for example, a He—Ne laser or a diode laser. In an exemplary embodiment, the laser source 33 can be a 635 nm, 658 nm, or 760 nm laser diode module. In such an embodiment, the laser source 33 can include fiber coupling optics and/or other components conventionally used to transmit laser energy emitted by a laser source through fiber optic hardware. As described above with respect to FIG. 1, the laser source 33a can be configured to generate and transmit monochromatic light towards the surface of the receptor 44.

The optical fiber 32 can be any type of glass or plastic fiber configured to guide light along its length by confining the light in a propagating form. The optical fiber 32 can be, for example, a single-mode or a multi-mode optical fiber, and the fiber 32 can be a graded-index fiber, a step-index fiber, a birefringent polarization-maintaining fiber, or a photonic crystal fiber.

As shown in FIG. 1a, the optical fiber 32 can connect the light source 33 directly to the collimator 42. In such an embodiment, the aperture 35, the objective 37 and/or the optical pinhole 39 discussed above with respect to FIG. 1, can be eliminated. It is understood that the beam transmitted from the optical fiber 32 can have essentially the same configuration as the beam emitted by the optical pinhole 39 of FIG. 1. Accordingly, using the optical fiber 32 can simplify the system 30a by eliminating the need for two or more separate elements requiring alignment.

The collimator 42 can take the place of the collimating lens 41 discussed above with respect to FIG. 1. The collimator can be any device configured to filter a stream of light rays such that only those traveling parallel to a specified direction are allowed through. The collimator 42 can be any type of collimator known in the art such as, for example, those made from refractive (lenses) or reflective (mirrors) optical elements.

The polarizer 43 is configured to intercept the collimated beam exiting the collimator 42. The polarizer 43 can be structurally similar to the polarizer 43 discussed above with respect to FIG. 1 and the polarizer 43 can be disposed substantially perpendicular to the laser line exiting the collimator 42. In an additional exemplary embodiment, the polarizer 43 can be disposed between the fiber 32 and the collimator 42. Disposing the polarizer 43 between, for example, the fiber 32 and the collimator 42 can reduce the potential for interference patterns in the resulting beam. It is understood that the polarizer 43 can also be angled slightly from a perpendicular orientation to further reduce interference patterns.

Figure 2A:
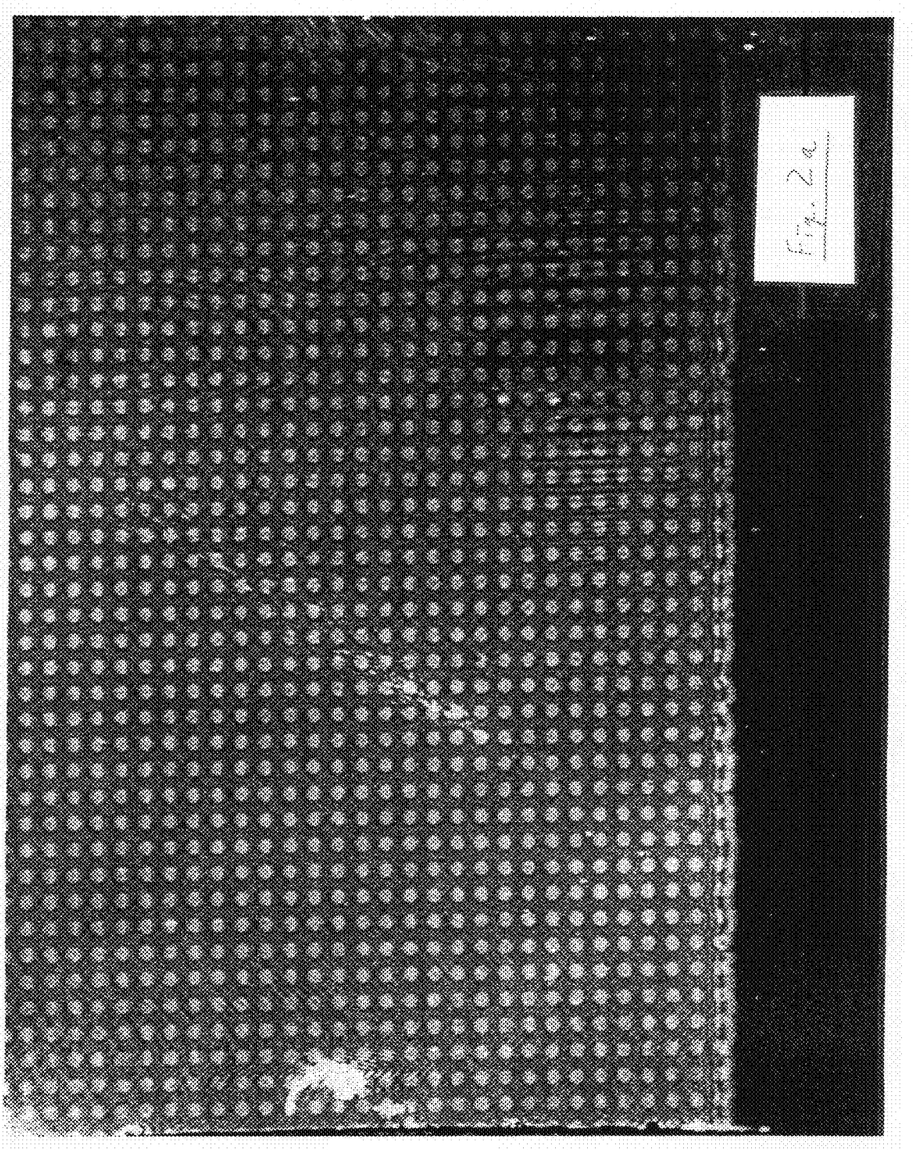
FIG. 2a illustrates a high density array according to an exemplary embodiment of the present disclosure.

The polarizer 43 is configured to direct a collimated polarized beam incident the receptor 44. The receptor 44 can be structurally similar to the receptor 44 discussed above with respect to FIG. 1. In the embodiments of FIGS. 1 and 1a, the receptor 44 can be configured to hold a micro-array of antibodies disposed on the coating of the substrate. The antibodies can be disposed in any array configuration known in the art and, in an exemplary embodiment, each antibody can be separated by approximately 100 microns on the coating of the substrate. The antibodies disposed on the coating of the receptor 44 can be selected for their ability to desirably attract and/or bond with bio-molecules that are put into contact therewith. In such an embodiment, potentially thousands of antibodies and/or other detection elements can be disposed on the receptor 44, and multiple disparate detection elements can be disposed on the same receptor 44. A sample of blood, urine, or other bio-molecular material can then be introduced to the micro-array of antibodies in a health care facility or laboratory. In such an embodiment, the system 30, 30a of the present disclosure can be configured to image the entire array of antibodies simultaneously. FIG. 2a is an image of an exemplary high-density array captured by the system 30, 30a of the present disclosure. Accordingly, a healthcare professional examining the array can be able to view thousands of data points from a single bio-molecular sample and can be able to diagnose multiple aspects of the bio-molecular sample in a single imaging application. Since multiple detection sites can be used on the receptor 44, redundant antibodies can be disposed thereon to reduce the risk of false positive readings. The imaging capabilities of the systems 30, 30a disclosed herein enable thousands of detection sites to be imaged simultaneously, and thus enable this redundancy. In particular, the high-density enabled by the systems 30, 30a greatly increases the information that can be obtained by the user. Known systems, on the other hand, are not capable of reading such small spots, and are typically limited to reading 5-10 detection total, making the cost of redundancy much higher. In addition, such known systems do not enable users to see the actual image, instead, the user merely sees a list of values corresponding to the parameter of interest for each target (such as, for example, concentration).

As shown in FIG. 1a, the laser line can reflect off of the receptor 44 and can intercept the fold mirror 46. The fold mirror can be any type of flat or substantially flat reflective surface known in the art. The fold mirror 46 can be configured to assist in folding the reflected image of the micro-array from the receptor 44 to the imaging optics 47a, 47b. It is also understood that illuminating the receptor 44 with the laser beam at the angle a may cause the resulting reflected image received by the fold mirror 46 to be compressed and/or otherwise deformed. For example, a 10 mm long receptor 44 can create a reflected beam 2-4 mm wide when incident at a highly oblique angle. Thus, tilting components of the system 30, 30a such as, for example, the detector 49 may compensate for the deformation of the resulting image. It is understood that folding the reflected image can allow greater design freedom, and can result in a system 30, 30a that is compact and easily handled relative to known systems.

The imaging optics 47a, 47b can be disposed downstream of the fold mirror 46 and can be mounted and/or otherwise configured such that a portion of the imaging optics 47a, 47b is substantially perpendicular to the laser line reflected from the fold mirror 46. The imaging optics 47a, 47b can be, for example, an Offner relay design comprising two nearly concentric spherical mirrors. The imaging optics 47a, 47b can be configured to relay images at approximately 1:1 magnification with very high resolution and low distortion. In an exemplary embodiment, the system 30, 30a can have a resolution of approximately 10 microns and can have substantially no measurable distortion. It is understood that, in an additional exemplary embodiment, the imaging optics 47a, 47b can comprise a much more complex system than what is depicted in FIG. 1a and in such an exemplary embodiment, the imaging optics 47a, 47b may comprise a complex configuration of mirrors and/or lenses configured to relay a high resolution image at low distortion.

The mirrors of the imaging optics 47a, 47b can be precisely aligned with respect to each other and with respect to, for example, the reflected multi-array such that the images presented to the detector 49 are limited only by diffraction. Imaging a collimated coherent source at an oblique incident angle with all reflective optics 47a, 47b can eliminate the potential for multiple reflections from within refractive lens elements. Accordingly, the systems 30, 30a disclosed herein may be significantly less expensive to manufacture as compared to known lens-based systems requiring highly specialized antireflective coatings.

It is understood that in coherent imaging systems, any dust/particles resident on optical surfaces can create fringe patterns. This may be especially true for reflective optics including mirrors where the scatter from the particle can be enhanced by a strong reflection from the underlying mirror. Accordingly, the systems 30, 30a disclosed herein can be assembled and/or sealed in a substantially dust-free environment so as to substantially eliminate contamination on the reflective optics and/or within surface coatings.

The detector 49 can be, for example, a CCD camera. In such an exemplary embodiment, the CCD camera can be board-mounted and a portion of the protective films and/or other devices causing interference with the imaging capabilities of the system 30a can be removed. As shown in FIG. 1a, the laser line is incident to the receptor 44 at an angle a, and the reflected object passes through multiple imaging planes. This configuration requires a relatively large depth of field in order for the image of the entire receptor 44 to remain in focus. It is understood that the depth of field can be defined as the distance along the optical axis (along the laser line) over which the desired object will be in sharp focus. The Offner relay defined by the imaging optics 47a, 47b is configured to tolerate this condition and the depth of field is extended by tilting the detector 49 at the angle b relative to the beam received from the imaging optics 47a, 47b.

It is understood that if the detector 49 was disposed perpendicular to the beam received from the imaging optics 47a, 47b, only the center of the receptor 44 would be in focus, and the image would blur toward the close and far edges of the receptor 44. By tilting the detector 49 such that the detector 49 is aligned with the series of images carried by the received beam, each of the images can be brought into sharp focus. In addition, by illuminating the detector 49 at an angle, the system 30a is configured to take advantage of the Brewster angle of the image. It is understood that, at a single particular angle of incidence (Brewster's angle), light with a particular polarization cannot be reflected, and at angles near the Brewster angle, reflectance is quite low. The polarization that cannot be reflected at this angle is the polarization (p-wave or p-polarization) for which the electric field of the light waves lies in the same plane as the incident ray and the surface normal (i.e., the plane of incidence). In short, although tilting the detector 49 enables the entire receptor 44 to be in focus, such a configuration results in considerable reflective interference and poor optical coupling efficiency. To compensate for this, the system 30a can include, for example, a polarization rotator, a waveplate, and/or other like structure (not shown) to rotate the polarization of the imaged light by 90 degrees. Through such rotation, the imaging angle would be sufficiently close to the Brewster angle such that highly efficient coupling and enhanced sensitivity could be obtained.

The image display system 30, 30a of the present disclosure can be used in a variety of different environments to assist in diagnosis of different medical conditions. For example, diagnostic chips can be examined using the system 30, 30a and the chips can be analyzed for, among other things, a given disease state, a function or dysfunction of a specific organ system, and a triage diagnostic in a first responder setting. The chips can also be used in a deployed environment with a portable system 30, 30a.

In additional embodiments of the present disclosure, the diagnostic chips can be used in, for example, immunodiagnostic assays, proteomics applications, and nucleic acid detection. For example, in immunodiagnostic testing, antibodies can be used as selectivity elements. In such testing, target molecules can include cytokines, chemokines, coagulation factors, plasma proteins, membrane and integral proteins, cytoplasmic and nuclear proteins, non-human proteins, peptides, plasma factors, small molecules, carbohydrates, and lipids. The aforementioned molecules are commonly found in bodily fluids, exudates, secretions, tissue samples, and serum. Commercial antibodies are available for the preceding targets and can be readily incorporated into the diagnostic chips of the present disclosure.

In further exemplary embodiments of the present disclosure, recombinant or native proteins or protein fragments can be used as selectivity elements. In such proteomic applications, target molecules can include: cytokines, chemokines, coagulation factors, plasma proteins, membrane and integral proteins, cytoplasmic and nuclear proteins, non-human proteins, peptides, plasma factors, small molecules, carbohydrates, and lipids. The aforementioned molecules are commonly found in bodily fluids, exudates, secretions, tissue samples, and serum.

In still another exemplary embodiment of the present disclosure, complementary cDNA, DNA, RNA, and rRNA molecules can be used as selectivity elements. In such nucleic acid detection applications, the target molecules can include genomic, ribosomal, messenger, transcript, and ribozymal nucleic acid sequences. The label-free nature of this technique allows all these measurements to be performed in a highly multiplexed format, rapidly, and with minimal cost.

For example, FIGS. 2a and 2c illustrate images acquired for a known standard sample receptor array. As seen in FIGS. 2a and 2c, it is not possible to acquire non diffraction-contaminated images using known image display systems, such as the systems described in Miller et al. FIGS. 2a and 2c illustrate images obtained using a known system having a sample array simulating receptor comprised of a silicon wafer with varying thicknesses of the antireflective layer simulating arrayed probe functionalization.

FIGS. 2b and 2d, on the other hand, illustrate images of the same standard sample acquired using the system 30, 30a of the present disclosure. As illustrated in FIGS. 2b and 2d, the system 30, 30a allows for precise intensity determination of array elements disposed on receptor 44. In particular, the system 30, 30a effectively removes spurious interference fringes intrinsic within the images obtained by known systems. The removal of the higher order interference fringes allows for detection of subtle reflectance changes within the array elements contained within receptor 44 that are directly related to the ultimate sensitivity of the technique implemented by the present system 30, 30a. Thus, quantitative detection of biomolecules is possible in the present system 30, 30a, wherein such detection was not possible with existing systems. In addition to allowing accurate quantitative data to be collected, the present system 30, 30a allows smaller spots to be imaged at a relatively high image density, such as, for example, imaging an array of spots 100 micron in diameter that are separated by approximately 100 microns. As discussed above, an image of such an exemplary high-density array is shown in FIG. 2a. It is understood that the spot size is only limited by the wavelength of light. Thus, imaging spots that are approximately 1 micron or slightly less in diameter is possible with the system 30, 30a even though arraying spots of this size may be difficult. This enables commercial arraying tools to be used to apply the detection spots. Few commercial technologies currently print the large spots that are required by known systems.

Figure 3:
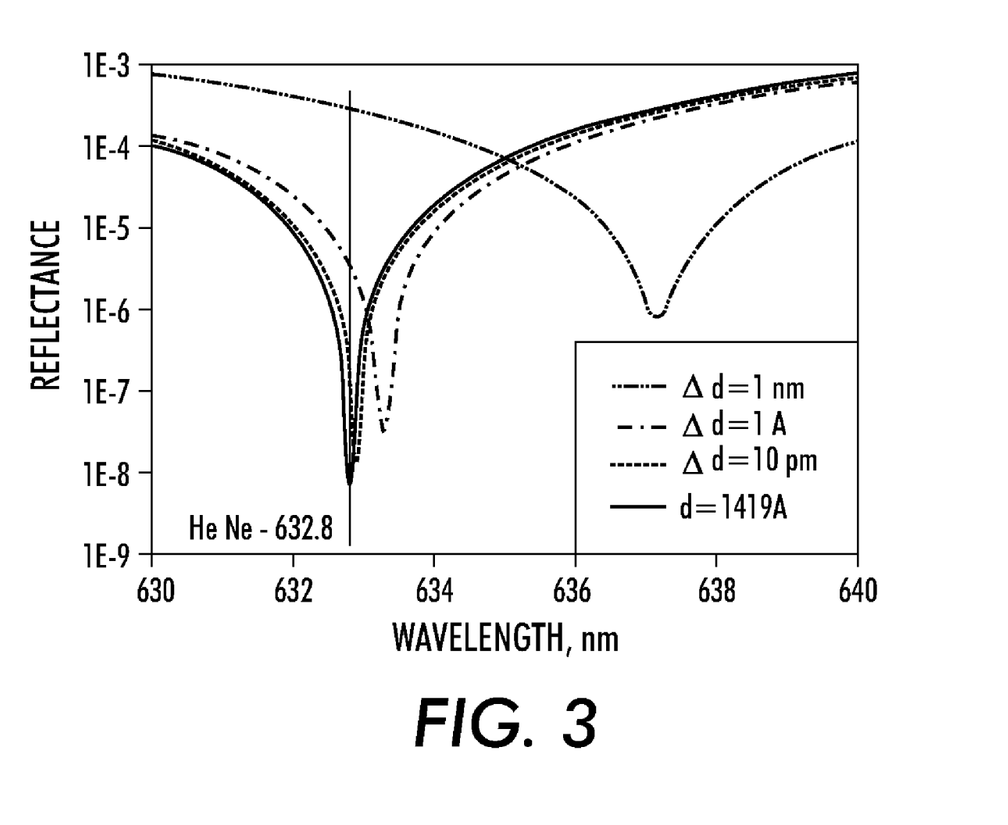
FIG. 3 reports a more detailed theoretical simulation of the expected sensitivity of the present device.

FIG. 3 illustrates a more detailed theoretical simulation of the expected sensitivity of the present system 30, 30a. The reflected signal increases nearly 1000 fold with the addition of a single angstrom of material. This level of sensitivity is not achievable in known devices.

Other embodiments of the disclosed image display system 30, 30a will be apparent to those skilled in the art from consideration of this specification. It is intended that the specification and examples be considered as exemplary only, with the true scope of the invention being indicated by the following claims.

What is claimed is:

1. A method of sensing at least one target on a receptor having a substrate and a translucent coating, the method comprising:
   (a) passing a reflected beam through compensation optics intermediate the receptor and a detector; and
   (b) minimizing interference patterns in an image of the target formed with the reflected beam.

2. The method of claim 1, further comprising illuminating the target with coherent light.

3. The method of claim 1, further comprising illuminating the target with a collimated beam.

4. The method of claim 1, further comprising illuminating the target with a polarized beam of narrow-bandwidth light.

5. The method of claim 1, further comprising employing a charge coupled device as the detector.

6. The method of claim 1, further comprising locating an aperture optically intermediate a source of an illumination beam and a detector, the receptor being optically intermediate the source of the illumination beam and the detector.

7. The method of claim 1, further comprising locating a spatial filter optically intermediate a source of an illumination beam and the receptor.

8. The method of claim 7, further comprising including an objective lens and an optical pinhole in the spatial filter.

9. The method of claim 8, further comprising including a plurality of lenses in the objective lens.

10. The method of claim 1, further comprising removing a p-wave component from an illumination beam impinging the target, and rotating polarization of the illumination beam optically upstream of the detector.

11. The method of claim 1, wherein minimizing interference patterns comprises removing fringe patterns from the image of the target.

12. The method of claim 1, further comprising expanding a diameter of an illumination beam impinging the target such that the expanded diameter is substantially equal to a length of the substrate.

13. The method of claim 12, wherein the expanded beam has a uniform intensity.

14. The method of claim 1, further comprising focusing a diverging illumination beam reflected by the receptor.

15. A method of sensing at least one target on a receptor having a substrate and a translucent coating, the method comprising:
   (a) passing a reflected beam through compensation optics intermediate the receptor and a detector; and
   (b) compensating for diffraction effects in an image of the target formed with the reflected beam.

16. The method of claim 15, further comprising illuminating the target with coherent light.

17. The method of claim 15, further comprising illuminating the target with a collimated beam.

18. The method of claim 15, wherein the compensation optics comprises an Offner relay.

19. The method of claim 15, further comprising employing a charge coupled device as the detector.

20. The method of claim 15, further comprising locating an aperture optically intermediate a source of an illumination beam and a detector.

21. The method of claim 15, further comprising locating a spatial filter optically intermediate of a source of an illumination beam and the receptor.

22. The method of claim 21, further comprising including an objective lens and an optical pinhole in the spatial filter.

23. The method of claim 22, further comprising including a plurality of lenses in the objective lens.

24. An apparatus for imaging a receptor on a substrate having a translucent coating, the apparatus comprising:
   (a) a coherent light source generating a coherent beam along a beam path;
   (b) a receptor disposed in the beam path to reflect the beam, the receptor forming a reflected beam along the beam path;
   (c) a detector located in the beam path to image the reflected beam, the detector being mounted at an oblique angle relative to the reflected beam received by the detector; and
   (d) compensation optics in the beam path optically intermediate the receptor and the detector.

25. The apparatus of claim 24, wherein the compensation optics includes a plurality of optical surfaces.

26. The apparatus of claim 24, further comprising an aperture optically intermediate the coherent light source and the receptor.

27. The apparatus of claim 24, further comprising a spatial filter optically intermediate the coherent light source and the receptor.

28. The apparatus of claim 27, wherein the spatial filter includes an objective and an optical pinhole.

29. The apparatus of claim 24, wherein the compensation optics comprises a component of an Offner relay.

30. The apparatus of claim 24, wherein the coherent beam is generated by the light source at an angle relative to the receptor.

31. The apparatus of claim 24, wherein the oblique angle is substantially equal to a Brewster angle of the detector.

* * * * *